US008079748B2

(12) United States Patent
Murakami

(10) Patent No.: US 8,079,748 B2
(45) Date of Patent: Dec. 20, 2011

(54) LIQUID AGITATING DEVICE

(75) Inventor: Miyuki Murakami, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 1048 days.

(21) Appl. No.: 11/518,095

(22) Filed: Sep. 8, 2006

(65) Prior Publication Data

US 2007/0002678 A1    Jan. 4, 2007

Related U.S. Application Data

(63) Continuation of application No. PCT/JP2005/004115, filed on Mar. 9, 2005.

(30) Foreign Application Priority Data

Mar. 10, 2004    (JP) .................................. 2004-067945

(51) Int. Cl.
*B01F 11/02*    (2006.01)
(52) U.S. Cl. ......................... 366/116; 366/118; 366/127
(58) Field of Classification Search .................. 366/117, 366/118, 120, 127, 116
See application file for complete search history.

(56) References Cited

U.S. PATENT DOCUMENTS

| 1,734,975 | A | * | 11/1929 | Loomis et al. ................... 516/38 |
| 2,620,894 | A | * | 12/1952 | Peterson et al. ................... 95/30 |
| 3,198,489 | A | * | 8/1965 | Finch ........................... 366/113 |
| 3,351,539 | A |   | 11/1967 | Branson |
| 4,584,475 | A | * | 4/1986 | Lao ............................... 250/332 |
| 4,602,184 | A |   | 7/1986 | Meitzler |
| 4,726,225 | A | * | 2/1988 | Brace et al. ................. 73/204.23 |
| 4,930,898 | A |   | 6/1990 | Miller-Ihli |
| 6,161,437 | A | * | 12/2000 | Brennan et al. ................. 73/655 |
| 6,777,245 | B2 | * | 8/2004 | Wixforth ...................... 436/180 |
| 2004/0115097 | A1 |   | 6/2004 | Wixforth et al. |
| 2008/0074945 | A1 | * | 3/2008 | Murakami et al. ............ 366/110 |

FOREIGN PATENT DOCUMENTS

| DE | 899 571 C | 12/1953 |
| DE | 195 34 955 A1 | 3/1996 |
| EP | 1 260 819 A1 | 11/2002 |
| JP | 36-7831 | 6/1961 |
| JP | 57 056031 A | 4/1982 |
| JP | 58 163425 A | 9/1983 |
| JP | 59 199025 A | 11/1984 |
| JP | H6-258328 | 9/1994 |
| JP | 2000-146986 | 5/2000 |
| JP | 2001-215232 | 8/2001 |
| WO | WO 02/081070 A1 | 10/2002 |

OTHER PUBLICATIONS

Shiokawa, Showko et al., "The Dynamics of SAW Streaming and its Application to Fluid Devices", Materials Research Society Symposium Proceedings (1995), pp. 53-64.
Supplementary European Search Report for Application No. EP05720386.1, dated Sep. 29, 2011, 5 pages.

* cited by examiner

*Primary Examiner* — David Sorkin
(74) *Attorney, Agent, or Firm* — Kilpatrick Townsend & Stockton LLP

(57) ABSTRACT

A liquid agitating device includes a sound wave generator that generates a sound wave; and a transmitting portion that transmits the sound wave generated by the sound wave generator, at least a portion of the transmitting portion being in contact with a liquid, and the transmitting portion emitting the sound wave towards the liquid at the portion in contact with the liquid. The sound wave emitted toward the liquid generates a local flow within the liquid and agitates the liquid.

39 Claims, 15 Drawing Sheets

LIQUID AGITATING DEVICE

CROSS-REFERENCE TO RELATED APPLICATIONS

This application is a continuation of PCT international application Ser. No. PCT/JP2005/004115 filed Mar. 9, 2005 which designates the United States, incorporated herein by reference, and which claims the benefit of priority from Japanese Patent Application No. 2004-067945, filed Mar. 10, 2004, incorporated herein by reference.

BACKGROUND OF THE INVENTION

1. Field of the Invention

The present invention relates to a liquid agitating device.

2. Description of the Related Art

A conventional agitating apparatus that agitates an agitated liquid with an agitator enhances an agitating effect and reduces agitating time by positioning a tip end of the agitator substantially at a middle level of the agitated liquid (see Japanese Patent Application Laid-Open No. H6-258328, for example). Further, a chemical analyzer that is provided with an ultrasound generator for agitating an agitated liquid with ultrasound has a piezoelectric transducer, being a ultrasonic generator, with separate electrodes, and drives control the separate electrodes so as to generate a sound wave with an appropriate intensity at an appropriate position for generation of swirling flow (see Japanese Patent Application Laid-Open No. 2001-215232, for example).

SUMMARY OF THE INVENTION

A liquid agitating device according to one aspect of the present invention includes a sound wave generator that generates a sound wave; and a transmitting portion that transmits the sound wave generated by the sound wave generator, at least a portion of the transmitting portion being in contact with a liquid, and the transmitting portion emitting the sound wave towards the liquid at the portion in contact with the liquid. The sound wave emitted toward the liquid generates a local flow within the liquid and agitates the liquid.

A liquid agitating device according to another aspect of the present invention includes a sound wave generator that generates a sound wave; and a transmitting portion that receives and transmits the sound wave generated by the sound wave generator, and that is in contact with two substances having different levels of acoustic impedance. The transmitting portion has a portion that emits the sound wave toward a liquid contained in a container from a portion which is on a surface of the transmitting portion and which intersects with an interface between the substances in contact with the transmitting portion.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
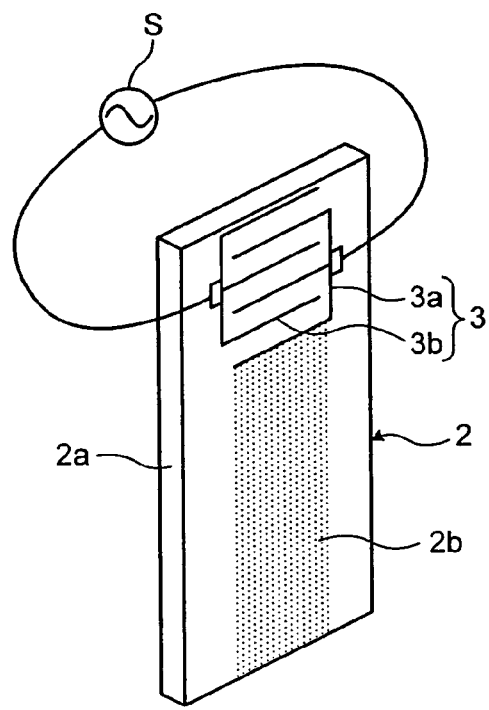
FIG. 1 is a schematic perspective view of a structure of an agitator including an IDT arranged on a piezoelectric substrate in a liquid agitating device according to a first embodiment.
Figure 2:
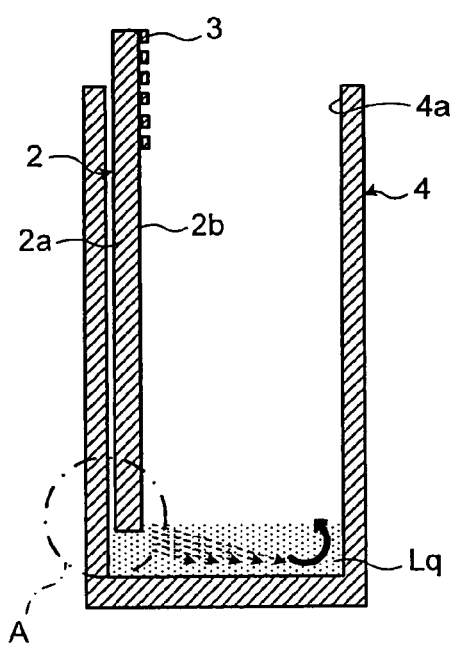
FIG. 2 is a diagram of the agitator placed inside a container containing a liquid for use.
Figure 3:
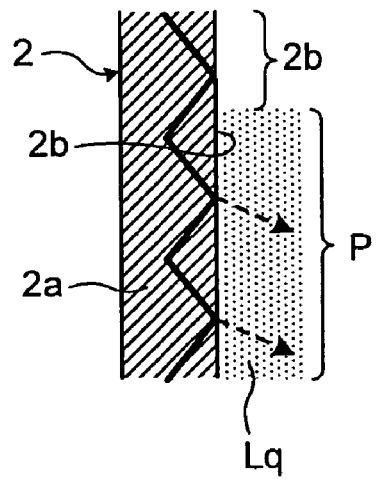
FIG. 3 is an enlarged view of a portion A of FIG. 2.
Figure 4:
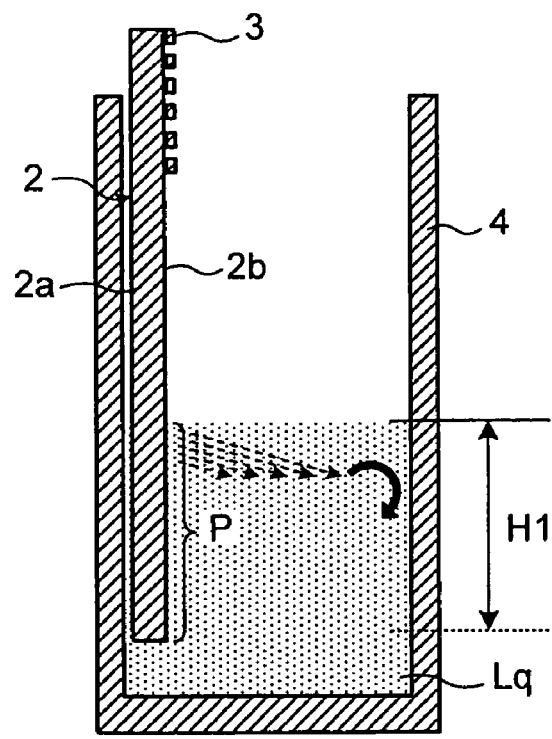
FIG. 4 is an explanatory diagram illustrating an effect of an increased amount of a target liquid inside the container which causes a change in liquid level.

A liquid agitating device according to a first embodiment of the present invention will be described in detail below with reference to the accompanying drawings. FIG. 1 is a perspective view showing a schematic structure of an agitator which includes an IDT arranged on a piezoelectric substrate in the liquid agitating device. FIG. 2 shows how the agitator is arranged during use inside a container which has a predetermined capacity and contains liquid. FIG. 3 is an enlarged view of a portion A of FIG. 2. FIG. 4 illustrates an effect of an increased amount of target liquid in the container which causes a change in liquid level.

An agitator 2 has, as shown in FIG. 1, a piezoelectric transducer 3 consisting of bamboo-blind-like or comb-shaped electrodes (i.e., IDT: Inter Digital Transducer) 3a and 3b in a transmitting portion 2b on a surface of a substrate 2a. The piezoelectric transducer 3 serves as a surface acoustic wave generator. The comb-shaped electrodes 3a and 3b receive an application of high-frequency alternating electric field from an alternating-current source S. As shown in FIG. 2, the agitator 2 is inserted into a container 4 containing liquid Lq from an opening 4a of the container 4 so as to come into contact with the liquid Lq, while the piezoelectric transducer 3 is positioned above the liquid Lq in a direction of gravitational force or at such a position that the piezoelectric transducer 3 does not come into contact with the liquid Lq. The agitator 2 is sufficiently long so that at least the tip end thereof reaches a bottom surface of the container 4. The piezoelectric transducer 3 is manufactured by semiconductor manufacturing technique, and for example, the comb-shaped electrodes 3a and 3b each having teeth arranged a few micrometer pitch are placed alternately so that the interval between each tooth of one electrode and the adjacent tooth of another electrode is $\lambda/4$, where $\lambda$ is a wavelength of a generated surface acoustic wave.

In the present invention, the transmitting portion 2b is a portion that transmits the sound wave (surface acoustic wave) on the surface of the substrate. As shown in FIG. 3, at least a part of the transmitting portion 2b comes into contact with the liquid Lq and transmits the sound wave (surface acoustic wave) generated by the piezoelectric transducer 3 to the liquid Lq from a portion within the portion in contact with the liquid Lq. In the agitator 2, the transmitting portion 2b is a portion that transmits the sound wave (surface acoustic wave) and is formed on the surface of a substrate 2a. As shown in FIG. 3, the transmitting portion 2b includes a functioning portion P which comes into contact with the liquid Lq and which sends the sound wave (surface acoustic wave) generated by the piezoelectric transducer 3 to the liquid Lq at a portion in contact with the liquid Lq. When the term "substrate" is used in the description of the transmitting portion in the present invention, the term means a solid substrate of a material, such as silicon and glass, employed in the semiconductor manufacturing technique, or a layer, such as a metal layer and an insulating layer, on the solid substrate. The term "substrate", when employed in the description of the transmitting portion, also implies a piezoelectric solid substrate of lithium niobate crystal, zinc oxide, or lead zirconate titanate (PZT), for example. Further, the term "substrate" also implies an element formed with a quartz layer or a metal layer, for example, deposited on a portion of the piezoelectric substrate, or a wall surface of the container 4.

An action of the agitator 2 will be described with reference to FIGS. 2 and 3. As shown in FIG. 2, the agitator 2 is inserted into the container 4 from the opening 4a of the container 4 and brought into contact with the liquid Lq contained in the container. Here, the agitator 2 is sufficiently long so that at least the tip end of the agitator 2 comes into contact with the liquid Lq. While the agitator 2 is held in the state of FIG. 2, electricity is supplied, for example, a high-frequency alternating electric field of approximately a few MHz to a few hundred MHz is applied to the piezoelectric transducer 3. When resonance condition is substantially met, i.e., when the frequency is substantially equal to a ratio of the speed of surface sound wave to the interval ($\lambda/4$) between the electrodes 3a and 3b of the piezoelectric transducer 3, surface acoustic wave is induced in a piezoelectric region of the substrate 2a.

A direction of propagation of the induced surface acoustic wave is equal to the direction of arrangement of the comb-shaped electrodes 3a and 3b engaged with each other. As shown in FIG. 3, the surface acoustic wave propagates along a surface of the substrate 2a at the side of the piezoelectric transducer 3. When the surface acoustic wave comes close to an air-liquid interface where the substrate 2a contacts with the liquid Lq, the surface acoustic wave is released to the liquid Lq, which is to be agitated, in a direction as shown by a dotted line and propagates through the liquid Lq. In general, when the acoustic impedance of the solid substrate is largely different from the acoustic impedance of the fluid in contact with the solid substrate, the surface acoustic wave is confined in a region approximately one wavelength deep from the surface of the solid substrate and advances in the propagation direction, whereas when the acoustic impedance of the solid substrate is close to the acoustic impedance of the fluid in contact therewith, the surface acoustic wave leaks out from the solid substrate to the side of the fluid. In other words, when an interface of two substances with different levels of acoustic impedance, for example, an air-liquid interface is brought into contact with the solid substrate, i.e., the transmitting portion, the energy of the surface acoustic wave propagates to a substance with higher acoustic matching with the solid substrate.

With respect to the agitator 2, at an upper portion of the substrate 2a, the fluid in contact with the substrate 2a is an atmosphere (air) represented by air or atmospheric air, which is present at the agitation, and hence the acoustic impedance of the solid substrate is largely different from the acoustic impedance of the fluid. Therefore, the surface acoustic wave propagates within the surface of the substrate 2a, i.e., within the transmitting portion 2b in a portion which is in contact with the air and located above the level of the liquid Lq. On the other hand, when the fluid in contact with the substrate 2a is the liquid Lq, i.e., the substance to be agitated, the acoustic impedance of the solid substrate is relatively close to the acoustic impedance of the fluid. Hence, in the agitator 2, at a portion where the substrate 2a is in contact with the liquid Lq, i.e., where the agitator 2 is in the liquid Lq, the surface acoustic wave undergoes a mode conversion to become a longitudinal wave and is leaked out to the side of the liquid Lq. As shown in FIG. 2, thus, the agitator 2 generates a local flow shown by an anticlockwise arrow by the longitudinal wave which is generated by the mode conversion and leaked out to the liquid Lq side as indicated by a dotted line, thereby agitating the liquid Lq.

Inside the transmitting portion 2b, the acoustic impedance gradually decreases from the portion with the piezoelectric transducer 3 towards the portion emitting the sound wave to the liquid. A relation $IT \geq IB \geq IL \gg IA$ is satisfied, where the acoustic impedance of the transmitting portion 2b is IB, the acoustic impedance of the liquid Lq is IL, the acoustic impedance of the air is IA, and the acoustic impedance of the piezoelectric transducer 3 is IT. Further, in the transmitting portion 2b, a difference between the acoustic impedance of the air and the acoustic impedance of the portion of the transmitting portion 2b in the air is larger than a difference in the acoustic impedance of the liquid Lq and the portion of the transmitting portion 2b in the liquid Lq. Still further, transmissivity of the sound wave in the propagation direction in the portion that emits the sound wave towards the liquid Lq is higher than the transmissivity of the sound wave in the portion in the air where the sound wave is leaked out into the air in the transmitting portion 2b.

A transverse wave such as surface acoustic wave cannot propagate in the fluid such as liquid. Therefore, at the interface between the agitator 2 and the liquid, the mode conversion occurs to convert the transverse wave into the longitudinal wave according to the Snell's law cited below:

$$\sin \theta_i / V_s = \sin \theta_{lt} / V_l \quad (1)$$

where $\theta_i$ is an incident angle of the surface acoustic wave which is incident on the interface between the agitator 2 and the fluid, $\theta_{lt}$ is an angle of transmission of the longitudinal wave which transmits through the fluid or is leaked out into the fluid, $V_s$ is acoustic velocity of the surface acoustic wave in the agitator 2, and $V_l$ is acoustic velocity of the longitudinal wave in the fluid.

Here, the mode-converted longitudinal wave is transmitted into and propagates through the liquid Lq from the agitator 2. A portion where the surface acoustic wave leaks out from the agitator 2 to the liquid Lq side is located immediately below the liquid level near the air-liquid interface and is a surface (functioning portion P) of the substrate 2a. Hence, the mode-converted longitudinal wave can efficiently cause the fluctuation in the air-liquid interface. For example, if the mode-converted longitudinal wave is approximately a few MHz to a few hundred MHz, the agitator 2 can generate a flow in the liquid Lq or the fluctuation in the air-liquid interface. On the other hand, when the mode-converted longitudinal wave is a repeating sound wave of pulses of approximately a few milliseconds to a few ten milliseconds, the agitator 2 can utilize an effect of acoustic radiation pressure to generate the fluctuation in the air-liquid interface, whereby the agitator 2 can agitate the liquid Lq by a vortex flow generated collaterally. Further, if the mode-converted longitudinal wave is a successive sound wave of at least a few ten milliseconds or more, the agitator 2 can generate a sound flow in the liquid Lq to agitate the liquid Lq.

Figure 5:
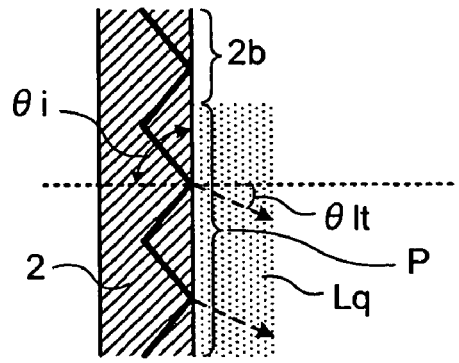
FIG. 5 is a diagram showing a relation between an incident angle of a surface acoustic wave which is incident on an interface between the agitator and fluid, and an angle of transmission of a longitudinal wave which transmits through and is leaked into the fluid.

According to the formula (1), the mode-converted longitudinal wave generated from the surface acoustic wave transmits through and leaks into the liquid while forming an angle $\theta_{lt}$ with respect to the agitator 2 as shown in FIG. 5. When the surface acoustic wave is a Rayleigh wave, $\theta_i=90°$. Since an angle of transmission and leakage is determined by the ratio of acoustic velocities ($V_l/V_s$), the longitudinal wave can be made to be emitted in a desired advance direction through a suitable selection of the acoustic velocity of the surface acoustic wave in the agitator 2.

In the agitator 2, the portion where the surface acoustic wave leaks out from the substrate 2a to the liquid Lq side is determined solely by the acoustic impedance of the fluid which has an interface in contact with the substrate 2a. Therefore in the agitator 2, as shown in FIG. 4, the functioning portion P where the surface acoustic wave leaks out from the substrate 2a to the liquid Lq side changes depending on the position of the air-liquid interface, in other words, depending on the amount of the liquid Lq. Therefore, even when the amount of liquid to be agitated significantly varies, for example, even when the air-liquid interface rises from the level shown in FIG. 2 to the level shown in FIG. 4 by a height H1, the agitator 2 can generate a local flow near the air-liquid interface and agitate the liquid Lq. As can be seen from the foregoing, the portion emitting the sound wave from the transmitting portion 2b to the liquid extends in the direction of gravitational force in the agitator 2. Therefore, the agitator 2 can function properly as far as at least a part of the transmitting portion 2b is in contact with the liquid Lq, without the need of adjustment of vertical positioning in accordance with the increase/decrease in the amount of liquid, and a position detector or a controller for positioning or the like is not necessary. Thus, the agitation of liquid can be achieved in a simple structure.

In addition, the agitator 2 of the first embodiment is advantageous in that (1) the strength of a force that works on the liquid to be agitated is adjustable based on the amplitude of the surface acoustic wave, (2) time of action, e.g., various lengths of pulse can be easily set electronically, (3) the agitator 2 can be controlled by software, (4) the agitator 2 can be easily cleansed since there is no unevenness in a portion to be immersed into the liquid, and (5) the agitator 2 can be easily held, for example, since the generation and the propagation of the surface acoustic wave occurs only in a region where the comb-shaped electrodes 3a and 3b of the piezoelectric transducer 3 intersect with each other.

Here, the agitator 2 can be modified and changed in various manners. For example, the piezoelectric transducer 3 may be provided not only on one side surface of the substrate 2 but also on another side surface of the substrate 2. Further, plural agitators may simultaneously be used at the agitation.

Figure 6:
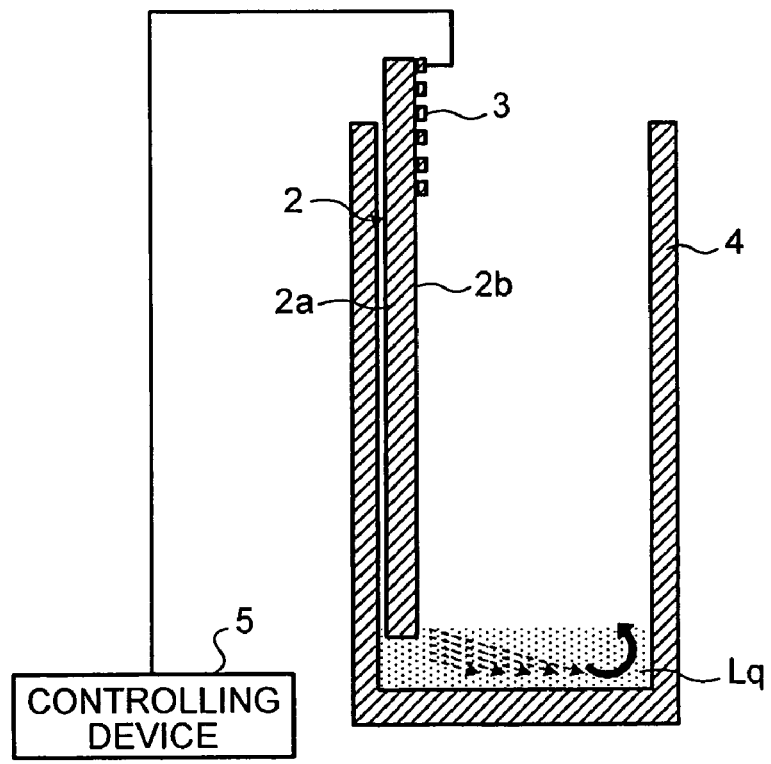
FIG. 6 is a diagram of a modification of the agitator according to the first embodiment.
Figure 7:
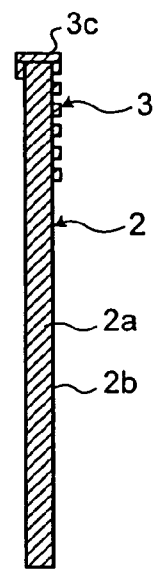
FIG. 7 is a diagram of another modification of the agitator according to the first embodiment.

Further, the piezoelectric transducer 3 of the agitator 2 may be controlled by a controlling device 5 as shown in FIG. 6. The controlling device 5 controls waveform, amplitude, time of application, timing of application, and the like of the high-frequency alternating electric field of approximately a few MHz to a few hundred MHz that is applied to the piezoelectric transducer 3, for example. The agitator 2 can realize efficient agitation by including the controlling device 5, and thereby providing an optimal driving vibration by suitably combining the parameters according to the type, the amount, or the like of the liquid to be agitated, for example. The piezoelectric transducer 3 may be provided with an extraction electrode 3c as shown in FIG. 7. Then, the agitator 2 can minimize the risk of damaging the transmitting portion 2b and facilitate the reception of the power supply.

Figure 8:
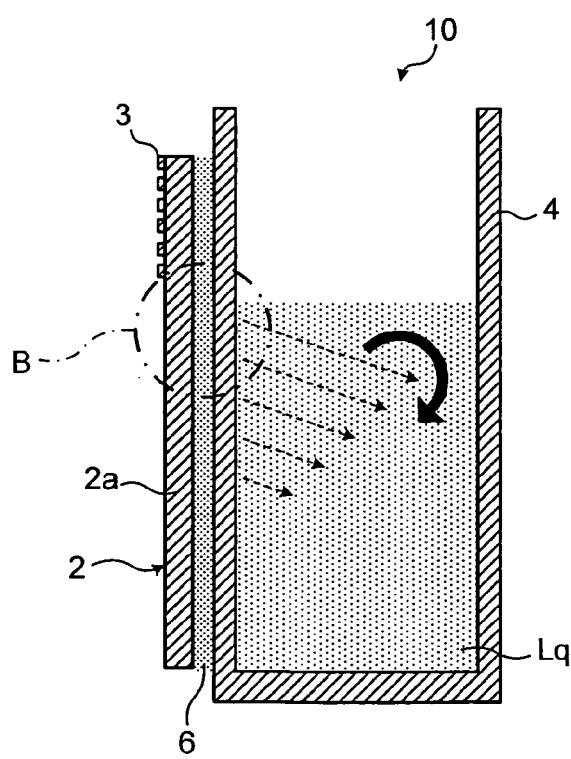
FIG. 8 is a schematic diagram of a basic structure of a liquid agitating device according to a second embodiment of the present invention.
Figure 9:
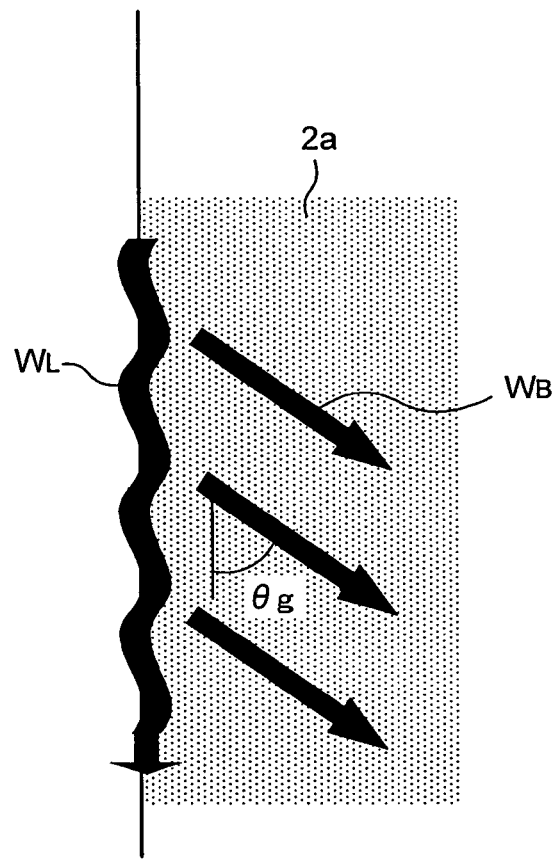
FIG. 9 is an enlarged view showing how leaky surface acoustic wave and bulk wave propagate in the liquid agitating device of FIG. 8.
Figure 10:
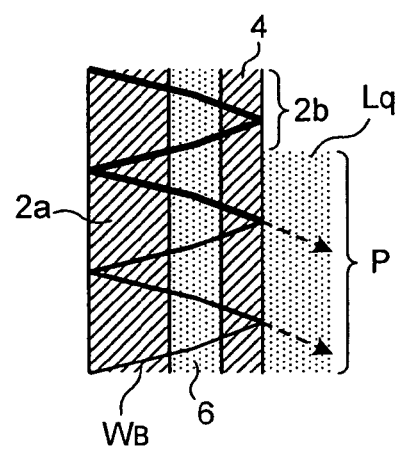
FIG. 10 is a diagram showing how waves propagate in a transmitting portion.
Figure 11:
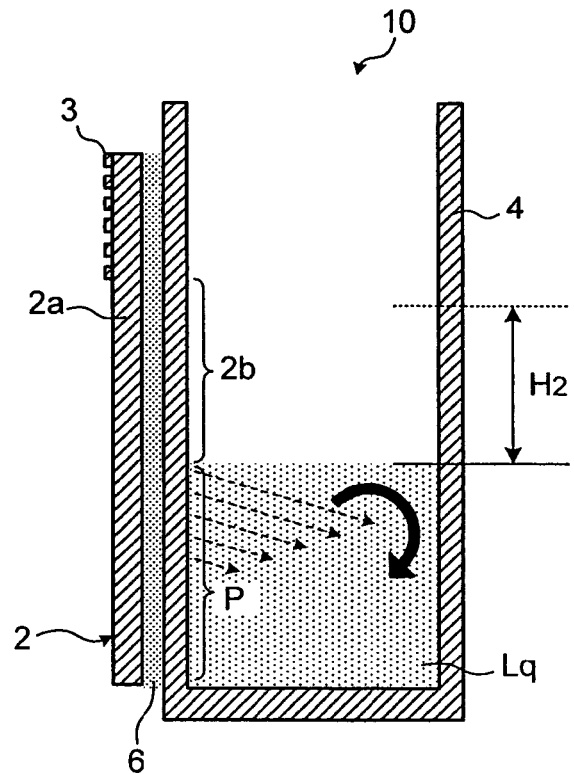
FIG. 11 is an explanatory diagram of an effect of an increased amount of the target liquid inside the container which causes a change in liquid level.

A liquid agitating device according to a second embodiment of the present invention will be described in detail below with reference to the accompanying drawings. FIG. 8 is a schematic diagram of a basic structure related with the liquid agitating device according to the second embodiment of the present invention. FIG. 9 is an enlarged view illustrating how leaky surface acoustic wave and bulk wave propagate in the liquid agitating device of FIG. 8. FIG. 10 shows how waves propagate in the transmitting portion. FIG. 11 illustrates an effect of an increased amount of target liquid in the container which causes a change in liquid level.

A liquid agitating device 10 according to the second embodiment, as shown in FIG. 8, includes an agitator 2, a container 4, and an acoustic matching layer 6. A substrate 2a, a wall surface of the container 4, and the acoustic matching layer 6 together form a transmitting portion. The agitator 2 is arranged close to a side surface of the container 4 with the acoustic matching layer 6 therebetween. The substrate 2a of the agitator 2 is made of a piezoelectric crystalline substrate of lithium niobate crystal, quartz, lithium tantalate, or the like and cut in an optimal crystal orientation. The piezoelectric transducer 3 is arranged on an opposite side from the side of the container 4 above the level of the liquid Lq, or at a level substantially the same as the level of the air-liquid interface of the liquid Lq. The acoustic matching layer 6 matches the agitator 2 and the container 4 with respect to the acoustic impedance. The acoustic matching layer 6 may be made of an adhesive agent such as epoxy resin, or shellac. Alternatively, the acoustic matching layer 6 may be gel or liquid.

It is desirable that the liquid agitating device 10 have such a structure that the acoustic impedance gradually decreases from the agitator 2, the acoustic matching layer 6, and the container 4 in this order, in other words, that the acoustic impedance of the transmitting portion that transmits the sound wave monotonously decreases towards a portion that emits the sound wave towards the liquid. With such a structure, the liquid agitating device 10 can minimize the loss of sound wave energy.

An action of the liquid agitating device according to the second embodiment will be described. In the liquid agitating device 10, a piezoelectric crystalline substrate which is a substrate of lithium niobate crystal cut in a specific crystal orientation is employed as the substrate 2a of the agitator 2. If the resonance condition is substantially satisfied, i.e., if the frequency is substantially equal to the ratio of the speed of surface sound wave to the distance between the comb-shaped electrodes 3a and 3b in the piezoelectric transducer 3 when the high-frequency alternating electric field of approximately a few MHz to a few hundred MHz is applied to the piezoelectric transducer 3, the leaky surface acoustic wave is induced in the agitator 2. As the leaky surface acoustic wave, wave propagation is known to concentrate its energy on the surface of the solid substrate similarly to the Rayleigh wave but emit the energy inside the substance as the bulk wave along with the propagation. FIG. 9 illustrates how the leaky surface acoustic wave WL and the bulk wave WB emitted along the propagation of the WL propagate in a portion B of FIG. 8.

The leaky surface acoustic wave propagates in a direction of arrangement of the comb-shaped electrodes 3a and 3b that engage with each other. The surface acoustic wave propagates towards the liquid to be agitated along the surface on the side of the piezoelectric transducer 3 in the liquid agitating device 10 of FIG. 8. On the other hand, the bulk wave WB is emitted towards inside the substrate 2a of the agitator 2 as shown in FIG. 9. An angle of advancement $\theta_g$ of the bulk wave WB depends on the crystal orientation of the cut substrate 2a. Hence, when the cut crystal orientation is selected so that the angle of advancement $\theta_g$ is an angle of total reflection, the bulk wave propagates through the substrate 2a, the acoustic matching layer 6, and the wall surface of the container 4 as the transmitting portion 2b as shown in FIG. 10. Here, if the acoustic impedance of the transmitting portion 2b and the acoustic impedance of the fluid Lq which is in contact with the wall surface of the container 4 are significantly different from each other, the bulk wave WB is confined in the transmitting portion during propagation. On the other hand, if the acoustic impedance of the transmitting portion and the acoustic impedance of the fluid Lq in contact with the wall surface of the container 4 are close with each other, the bulk wave WB leaks out from the functioning portion P of the wall surface of the container 4 towards the side of the fluid as shown by a dotted line in FIG. 10. The liquid agitating device 10 generates a clockwise local flow as shown by an arrow due to the bulk wave WB leaking out from the wall surface of the container 4 as shown by a dotted line in FIG. 8, thereby agitating the liquid Lq.

Since the transverse wave cannot propagate through the fluid like the liquid Lq, the mode conversion occurs from the transverse wave to the longitudinal wave according to the Snell's law as shown by the formula (1) at the interface between the wall surface of the container 4 and the liquid. In other words, the mode-converted longitudinal wave transmits and propagates from the wall surface of the container 4 to the liquid. Since the longitudinal wave transmits and propagates from the wall surface immediately below the liquid level of the container to the liquid, the mode-converted longitudinal wave can make the air-liquid interface efficiently fluctuate. For example, if the mode-converted longitudinal wave is approximately a few MHz to a few hundred MHz, the agitator 2 can generate a flow in the liquid Lq, or cause the fluctuation in the air-liquid interface. On the other hand, if the mode-converted longitudinal wave is a repeating sound wave of a pulse of approximately a few milliseconds to a few ten milliseconds, the agitator 2 can utilize the effect of acoustic radiation pressure to cause fluctuation in the interface, and agitate the liquid Lq with a vortex flow generated incidentally. Further, if the mode-converted longitudinal wave is a successive sound wave of at least a few ten milliseconds or more, the agitator 2 can generate a sound flow in the liquid Lq and agitate the liquid Lq.

Here, in the-liquid agitating device 10 according to the second embodiment, a portion where the longitudinal wave transmits to and propagates through the liquid from the wall surface of the container immediately below the liquid level depends only on the acoustic impedance of the fluid. Hence, in the liquid agitating device 10, the functioning portion P where the longitudinal wave transmits and propagates through the liquid from the wall surface of the container immediately below the liquid level changes according to the position of the air-liquid interface, i.e., the amount of the liquid Lq as shown in FIG. 11. Therefore, even when the amount of liquid to be agitated significantly changes, for example, even when the air-liquid interface drops from the level shown in FIG. 8 to the level of FIG. 11 by a height H2, the liquid agitating device 10 does not need to change the vertical position of the agitator 2. Therefore, the liquid agitating device 10 does not need a position detector and a controller for position control.

Further, the liquid agitating device 10 according to the second embodiment is advantageous in that (1) the strength of a force exerted to the liquid to be agitated is adjustable based on the amplitude of the leaky surface acoustic wave, (2) time of action, for example, various lengths of pulse can be easily and electronically set, (3) the liquid agitating device 10 can be controlled through software, and (4) there is no contamination attributable to the agitator 2 since the agitator 2 does not come into contact with the liquid to be agitated.

Figure 12:
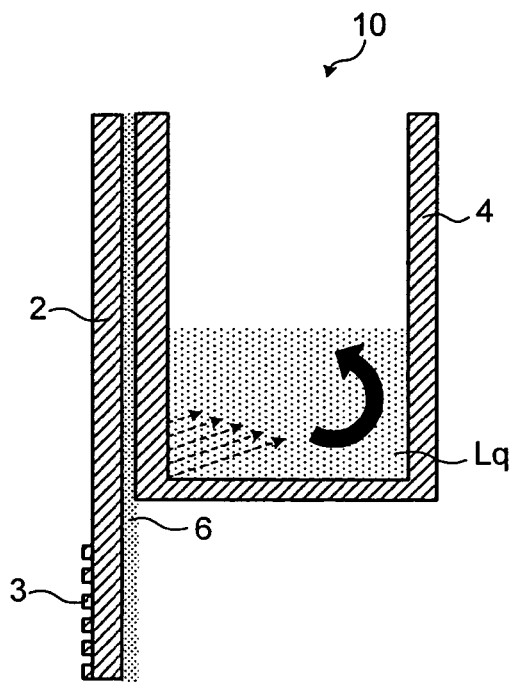
FIG. 12 is a diagram of a first modification of the liquid agitating device according to the second embodiment.
Figure 13:
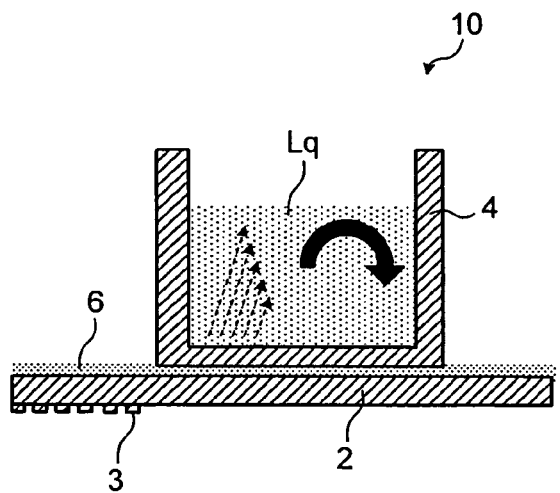
FIG. 13 is a diagram of a second modification of the liquid agitating device according to the second embodiment.
Figure 14:
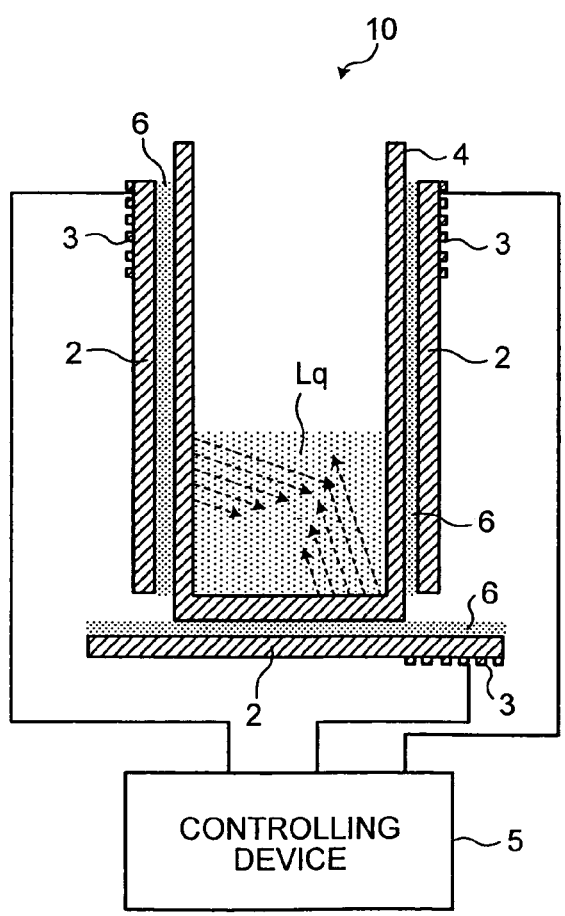
FIG. 14 is a diagram of a third modification of the liquid agitating device according to the second embodiment.

Further, the liquid agitating device 10 according to the second embodiment can be modified and changed in various manners. For example, the piezoelectric transducer 3 can be arranged in a lower portion of the agitator 2 at a lower level than the bottom surface of the container 4, depending on a design of the liquid agitating device 10, the direction of agitation of the liquid Lq, or the like as shown in FIG. 12. Further, the agitator 2 may be arranged so that the transmitting portion extends in the horizontal direction at the bottom surface of the container 4 as shown in FIG. 13, depending on the density of the liquid Lq to be agitated, the direction of agitation of the liquid Lq, and the like. In the examples as shown in FIGS. 12 and 13, the interface between the ambient gas and the container forms an interface of the two with different values of acoustic impedance. Further, the liquid agitating device 10 can efficiently agitate the liquid Lq by including plural agitators 2 on different wall surfaces of the container 4, and driving the plural piezoelectric transducer 3 at random by the controlling device 5 as shown in FIG. 14.

Figure 15:
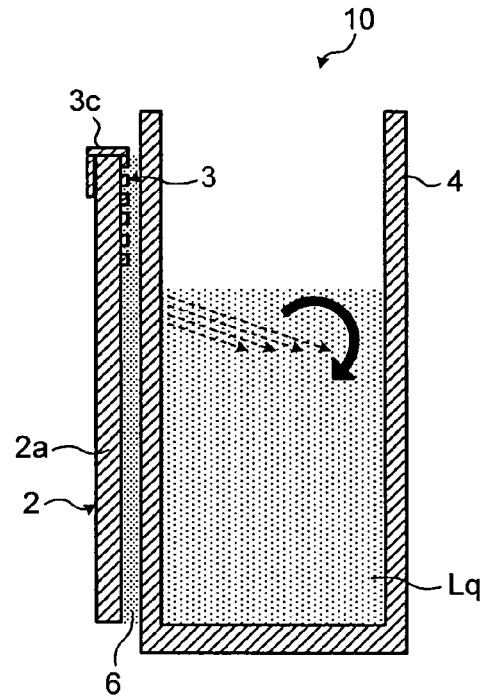
FIG. 15 is a diagram of a fourth modification of the liquid agitating device according to the second embodiment.

Here, while the piezoelectric transducer 3 is arranged at the container 4 side of the substrate 2a, the extraction electrode 3c may be provided as well in the agitator 2 as shown in FIG. 15. When the piezoelectric transducer 3 is arranged at the container 4 side, the transmission and propagation of the longitudinal wave through the liquid becomes faster compared with a device in which the piezoelectric transducer 3 arranged on an outer surface. Further, when the extraction electrode 3c is provided, the power can be easily supplied to the piezoelectric transducer 3. Here, if the agitator 2 is arranged in the vertical direction with respect to the container 4, a flow in the vertical direction is generated in the liquid. On the other hand, if plural agitators 2 are arranged on the wall surface of the container 4 in the horizontal direction, the longitudinal wave transmits and propagates in the horizontal direction in the liquid, and a flow of the horizontal direction is generated in the liquid. Hence, the plural agitators 2 may be arranged in various combinations depending on a desired flow to be generated.

Figure 16:
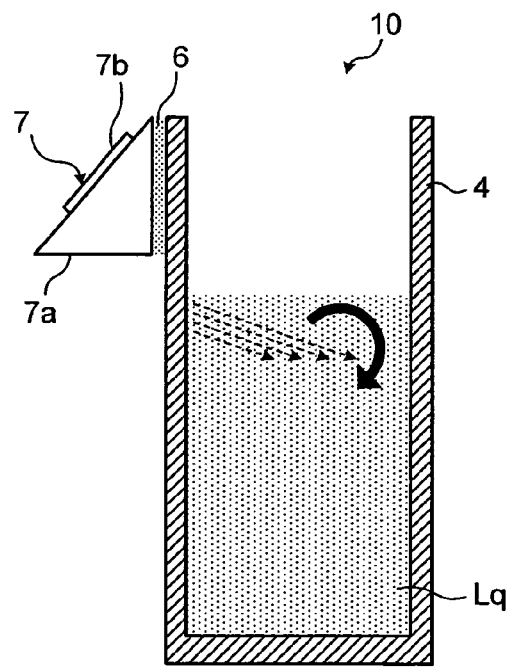
FIG. 16 is a diagram of a fifth modification of the liquid agitating device according to the second embodiment.
Figure 17:
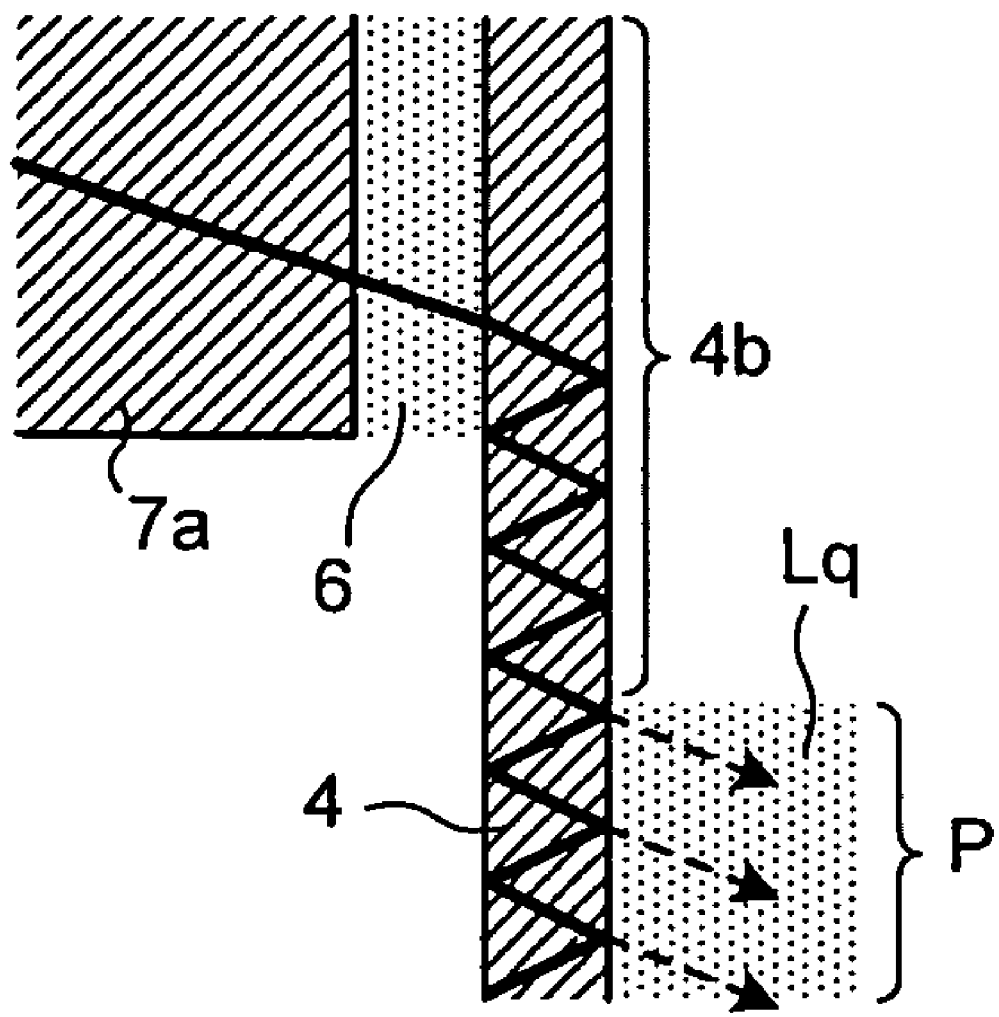
FIG. 17 is an enlarged view showing how the ultrasound is leaked out into the liquid from a functioning portion on a wall surface of the container in the liquid agitating device according to the fifth modification.

Further, the liquid agitating device 10 may include an agitator 7 as shown in FIG. 16 in place of the agitator 2 in which the piezoelectric transducer 3 is provided. In the agitator 7, an angle transducer 7b is attached to a wedge 7a, and ultrasound (longitudinal wave) generated by the angle transducer 7b may be totally reflected on the wall surface of the container 4. Thus, only the wall surface of the container 4 may serve as the transmitting portion 4b (see FIG. 17). Thus, the liquid agitating device 10 can generate a clockwise local flow in the liquid Lq by the ultrasound leaked out from the functioning portion P on the wall surface of the container 4 to the liquid Lq as shown by a dotted line in FIG. 17, to agitate the liquid Lq. Further, in the liquid agitating device 10 according to the second embodiment and the modifications thereof, the portion emitting the sound wave to the liquid is provided on a different surface from the surface on which the sound wave generator is provided. Therefore, the sound wave generator is even less likely to be brought into contact with the liquid.

Figure 18A:
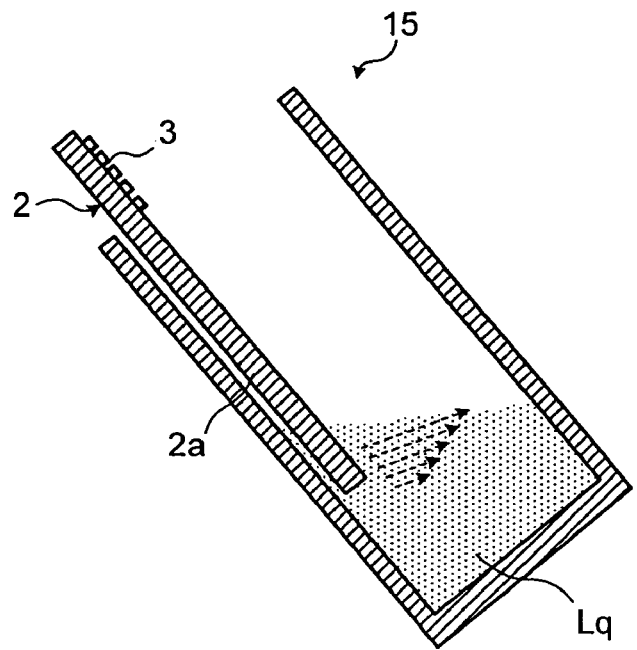
FIG. 18A is a schematic diagram showing a basic structure of a liquid agitating device according to a third embodiment.
Figure 18B:
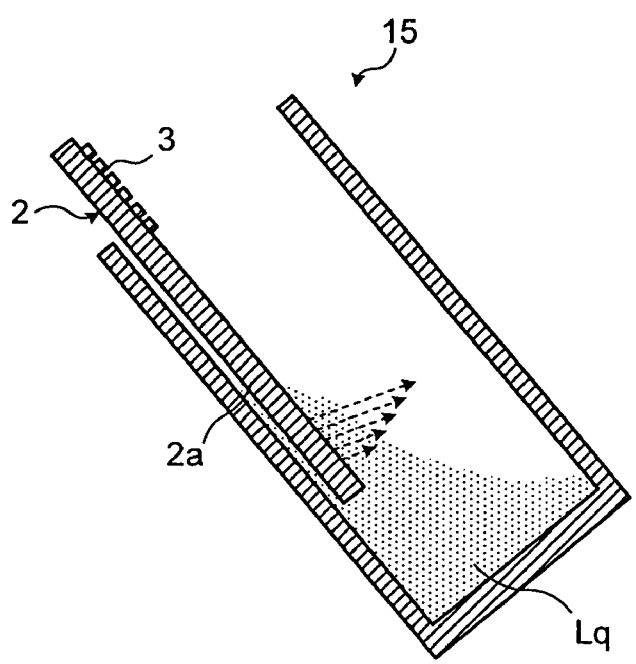
FIG. 18B shows an example of interface fluctuation caused by the liquid agitating device of FIG. 18A.
Figure 19:
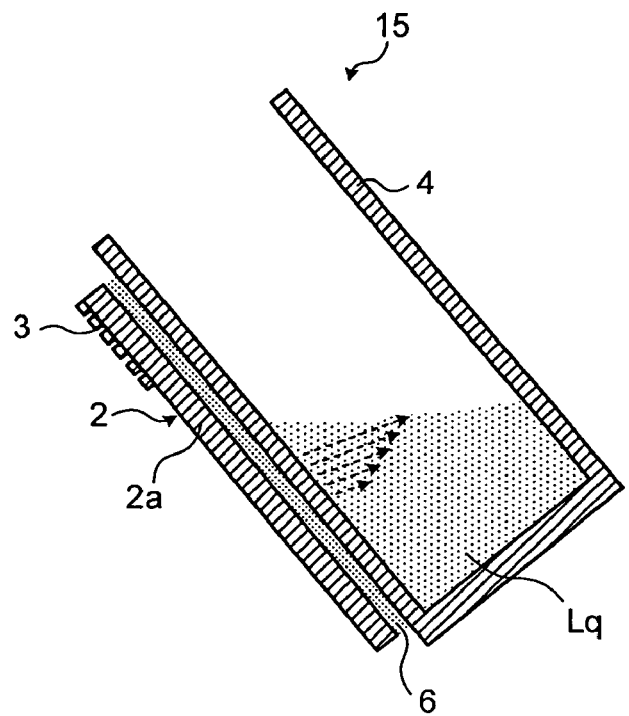
FIG. 19 is a schematic diagram of a first modification of the liquid agitating device according to the third embodiment.
Figure 20:
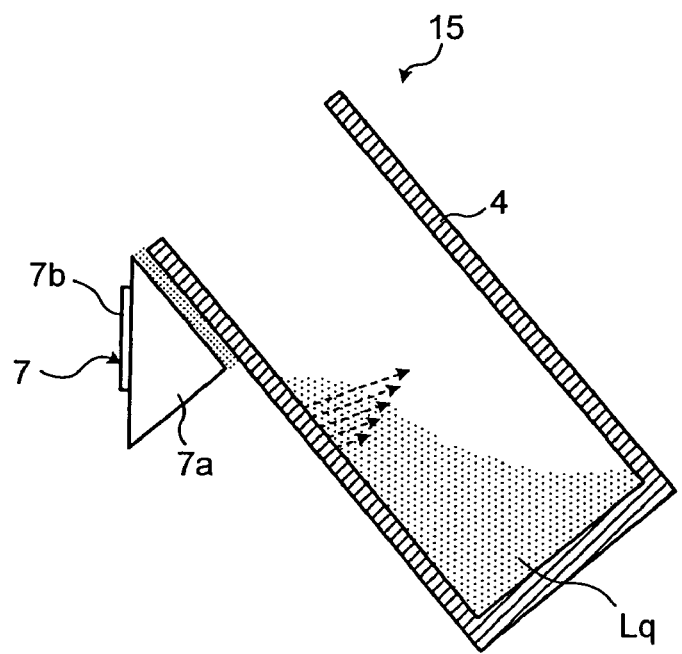
FIG. 20 is a schematic diagram of a second modification of the liquid agitating device according to the third embodiment.

A liquid agitating device according to a third embodiment of the present invention will be described in detail below with reference to the accompanying drawings. In the liquid agitating device according to the third embodiment, the container 4 is arranged at an angle. FIG. 18A is a schematic diagram showing a basic structure of the liquid agitating device according to the present invention wherein the agitator is brought into direct contact with the liquid for agitation. FIG. 18B shows an example of fluctuation in the interface caused by the liquid agitating device. FIG. 19 is a schematic diagram illustrating a first modification of the liquid agitating device according to the third embodiment. FIG. 20 is a schematic diagram illustrating a second modification of the liquid agitating device according to the third embodiment.

In a liquid agitating device 15, the agitator 2 is set in the container 4 which is tilted by a predetermined angle. Here, the surface acoustic wave generated by the piezoelectric transducer 3 of the agitator 2 undergoes the mode conversion at a portion where the substrate 2a is in contact with the liquid Lq to become a longitudinal wave. The mode-converted longitudinal wave transmits through and leaks out into the liquid while forming an angle $\theta_{lt}$ with respect to the agitator 2 according to the Snell's law. For example, provided that the surface acoustic wave is Rayleigh wave, the solid substrate is of lithium niobate, and the liquid Lq is water, then the angle $\theta_{lt}$ of transmission and leakage is approximately 22°.

Hence, if the agitator 2 and the container 4 are arranged at an angle of inclination which is larger than the angle $\theta_{lt}$ of transmission and leakage, i.e., larger than approximately 22°, the longitudinal wave having a vertically upward component as shown in FIG. 18A is emitted towards the liquid in a direction toward the air-liquid interface from the agitator 2 as shown by a dotted line. Therefore, the liquid agitating device 15 can facilitate the interface fluctuation compared with the device with the vertically arranged agitator 2 and container 4.

If the longitudinal wave is a repeating sound wave of pulses of approximately a few milliseconds, the interface of the liquid comes closer to the air-liquid interface side of the agitator 2 due to the effect of the acoustic radiation pressure. Thus, the portion which has been in contact with the air is brought into contact with the liquid. Hence, as shown in FIG. 18B, more fluctuation of the interface can be induced.

The liquid agitating device 15 can be modified and changed in various manners. For example, in the liquid agitating device 15, the agitator 2 may be arranged close to the side surface of the container 4 with the acoustic matching layer 6 therebetween in FIG. 19. Then, the transmitting portion may be formed with the substrate 2a, the wall surface of the container 4, and the acoustic matching layer 6. Further, in the liquid agitating device 15, the agitator 7 including the angle transducer 7b attached to the wedge 7a may be arranged on the wall surface of the container 4 as shown in FIG. 20.

Figure 21:
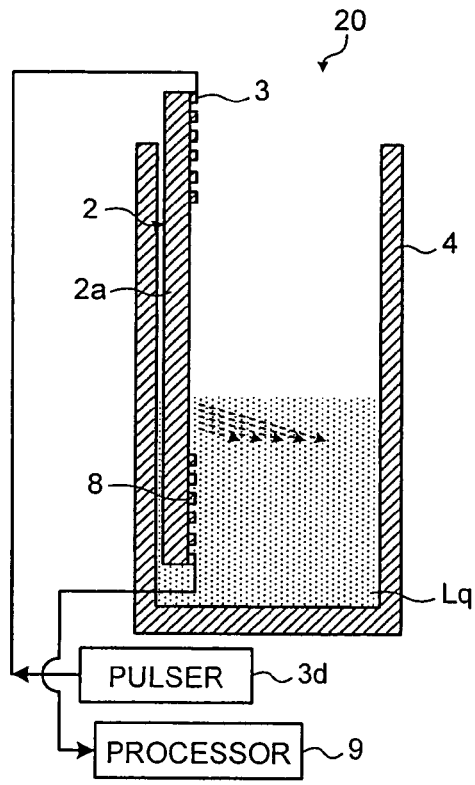
FIG. 21 is a schematic diagram of a liquid agitating device according to a fourth embodiment.
Figure 22:
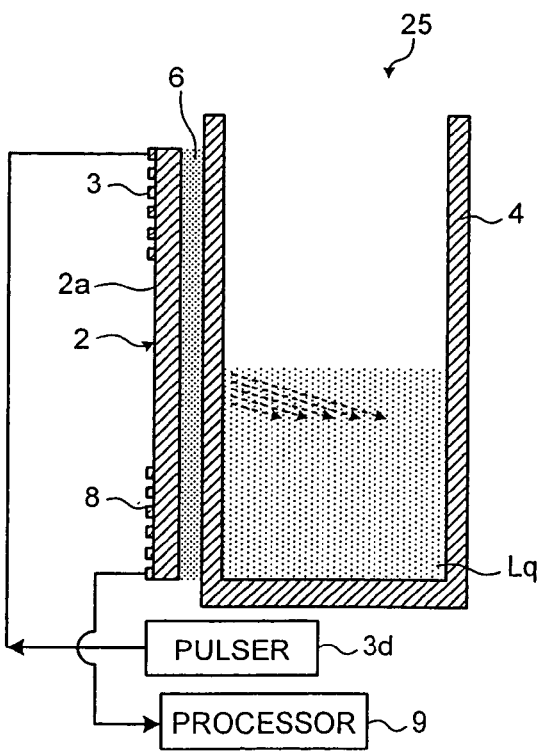
FIG. 22 is a schematic diagram of a modification of the liquid agitating device shown in FIG. 21.
Figure 23:
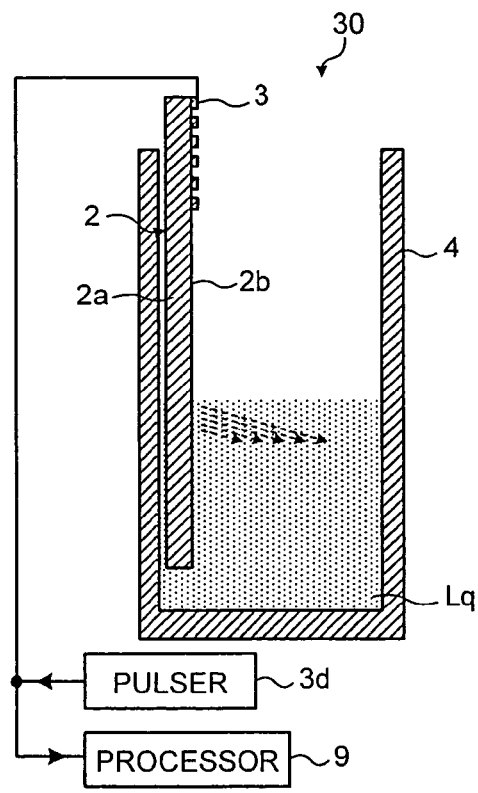
FIG. 23 is a schematic diagram of another modification.

A liquid agitating device according to a fourth embodiment of the present invention will be described below with reference to FIGS. 21 to 23. The liquid agitating device according to the fourth embodiment allows for a detection of presence and absence of the liquid inside the container 4. FIG. 21 is a schematic diagram of the liquid agitating device according to the fourth embodiment. FIG. 22 is a schematic diagram of a modification of the liquid agitating device shown in FIG. 21. FIG. 23 is a schematic diagram of another modification.

A liquid agitating device 20 includes the agitator 2 provided with a sound wave detector 8, a pulser 3d which makes the piezoelectric transducer 3 generate a pulse, and a processor 9 which processes a sound wave detected by the sound wave detector 8. The sound wave detector 8 has a similar structure as the structure of the piezoelectric transducer 3, and detects the surface acoustic wave generated by the piezoelectric transducer 3. The processor 9 processes signals output from the sound wave detector 8 and detects whether the agitator 2 comes into contact with the liquid Lq or not. Here, as described with reference to the first and the second embodiments, when the difference in the acoustic impedance of the agitator 2 and the acoustic impedance of the fluid in contact with the agitator 2 is significant, the surface acoustic wave generated by the piezoelectric transducer 3 in the liquid agitating device propagates within a region approximately one wavelength deep from the surface of the substrate 2a. On the other hand, when the acoustic impedance of the agitator 2 and the acoustic impedance of the fluid in contact with the agitator 2 are close to each other, the surface acoustic wave is leaked out to the side of fluid from the substrate 2a.

Here in the liquid agitating device 20, if the agitator 2 is not acoustically in contact with the liquid Lq in any portions, the surface acoustic wave generated by the piezoelectric transducer 3 advances through the substrate 2a to the liquid side and is detected by the sound wave detector 8. On the other hand, in the liquid agitating device 20, if the tip end of the agitator 2, or other portion located above the tip end in the agitator 2 comes into contact with the liquid Lq, the surface acoustic wave is leaked out from the agitator 2 to the fluid side, and hence the sound wave detector 8 does not detect anything.

Hence, with the use of the above described effect, the liquid agitating device 20 can be utilized as a detector that detects whether the liquid is in the container or not by detecting whether the agitator 2 is brought into contact with the liquid Lq or not. In the liquid agitating device 20, the sound wave detector 8 can be utilized for positioning of the agitator 2, so as to prevent collision of the agitator 2 with the bottom surface of the container 4, for example.

Further, in a liquid agitating device 25 shown in FIG. 22, the agitator 2 provided with the sound wave detector 8 is arranged outside the container 4 with the acoustic matching layer 6 therebetween. The liquid agitating device 25 can utilize the sound wave detector 8 as a detector to detect whether the container 4 is filled with the liquid Lq or not. On the other hand, a liquid agitating device 30 shown in FIG. 23 does not include the sound wave detector 8 in the agitator 2, for example. In the liquid agitating device 30, when a short pulse is applied to the piezoelectric transducer 3, the sound wave is reflected by an end face of the agitator 2 if the agitator 2 is not in contact with the liquid Lq, and an echo of the pulse sent from the piezoelectric transducer 3 can be detected with a predetermined time delay. Hence, the agitator 2 does not need to have the sound wave detector 8 as a separate element, and the agitator 2 can detect whether the liquid is in the container or not.

Figure 24:
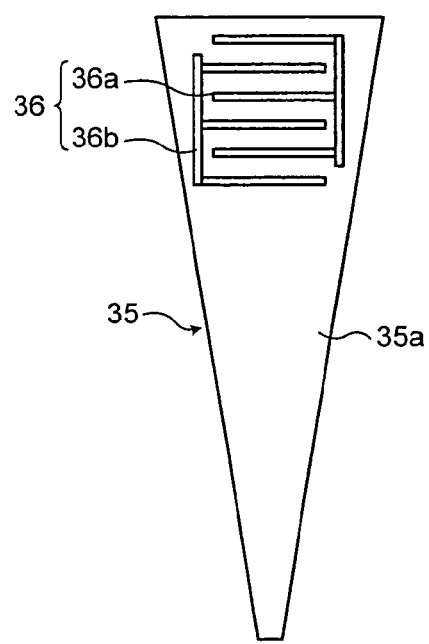
FIG. 24 is a front elevational view of a liquid agitating device according to a fifth embodiment.
Figure 25:
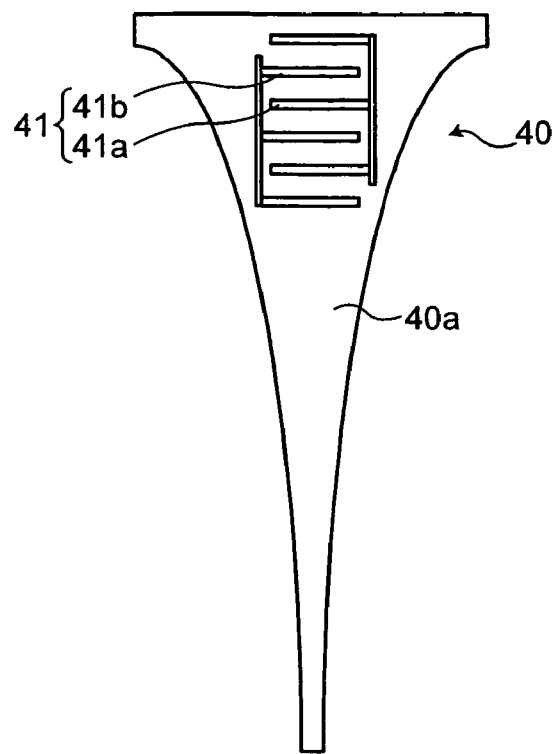
FIG. 25 is a front elevational view of a modification of an agitator shown in FIG. 24.

A liquid agitating device according to a fifth embodiment of the present invention will be described in detail below with reference to the accompanying drawings. The liquid agitating device according to the fifth embodiment amplifies an output of the piezoelectric transducer and radiates the same to the liquid. FIG. 24 is a front elevational view of an agitator having a substrate which is so formed that the width thereof gradually decreases toward a tip end. FIG. 25 is a front elevational view of a modification of the agitator shown in FIG. 24.

The agitator 35 is formed so that lengths of comb-shaped electrodes 36a and 36b of a piezoelectric transducer 36 are fixed, while width of a substrate 35a decreases in a linear manner toward a tip end as shown in FIG. 24. On the other hand, an agitator 40 is formed so that lengths of comb-shaped electrodes 41a and 41b of the piezoelectric transducer 41 are fixed, while width of a substrate 40a gradually decreases in an exponential manner toward a tip end. In the agitators 35 and 40, the surface acoustic waves generated by the piezoelectric transducer 36 and 41 are repeatedly reflected inside the substrates 35a and 40a during advancement toward the tip end of the substrate 35a and 40a, respectively. Therefore, the resonance effect of the surface acoustic wave in the agitators 35 and 40 are enhanced, and the amplitude of the mode-converted longitudinal wave radiated towards the liquid can be amplified. Thus, the effect of liquid agitation can be enhanced. Further, since the width of the tip end portion from which the sound wave is emitted towards the liquid is narrower than the width of a portion where the piezoelectric transducer 36 is provided in the agitators 35 and 40, the agitators 35 and 40 can be employed even in a small container.

Figure 26:
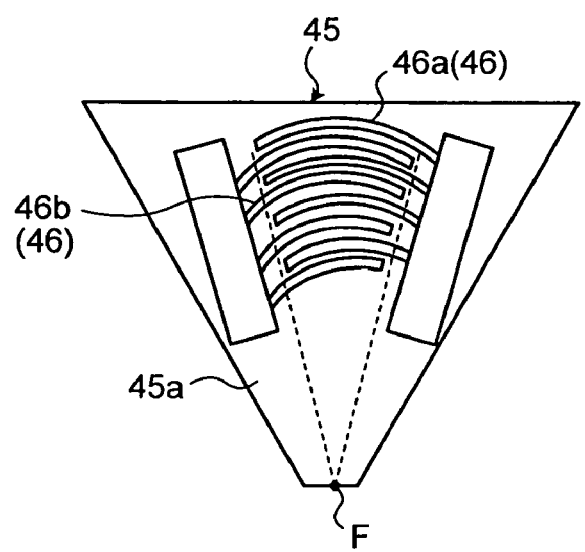
FIG. 26 is a front elevational view of another example of the liquid agitating device according to the fifth embodiment.
Figure 27:
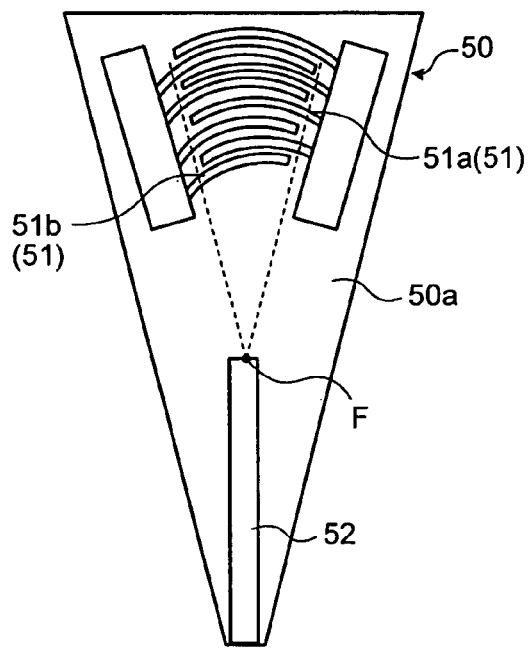
FIG. 27 is a front elevational view of still another example of the liquid agitating device according to the fifth embodiment.

Further, an agitator 45 shown in FIG. 26 is so formed that the width of a substrate 45a decreases towards a tip end in a linear manner, and comb-shaped electrodes 46a and 46b of a piezoelectric transducer 46 are formed in a circular arc shape. In the agitator 45, the curvature radius of each of the comb-shaped electrodes 46a and 46b is set so that the surface acoustic wave generated by the piezoelectric transducer 46 is focused on a point F at the tip end. On the other hand, in an agitator 50 shown in FIG. 27, a waveguide 52 is provided in a substrate 50a, and comb-shaped electrodes 51a and 51b are formed in a circular arc shape so that the surface acoustic wave generated by a piezoelectric transducer 51 is focused on a point F at an inlet of the waveguide 52. Hence, the agitators 45 and 50 can focus the surface acoustic wave generated by the piezoelectric transducers 46 and 51, respectively, at a predetermined position in the transmitting portion, to concentrate and amplify the energy of the surface acoustic wave on the point F, whereby the agitators 45 and 50 can radiate the longitudinal wave with extremely large amplitude to the liquid, thereby enhancing the effect of liquid agitation. Here, a metal or a groove may be used as the waveguide 52.

Here, the liquid agitating device according to the fifth embodiment may be employed for efficiently transmitting the sound wave to a minute portion, for example, for moving the fluid such as powder other than liquid, for transporting a minute particle such as a liquid droplet and cell, other than for agitating the liquid. In terms of sound wave focusing, it is preferable that the width of the transmitting portion decrease at least constantly, or monotonously.

Figure 28:
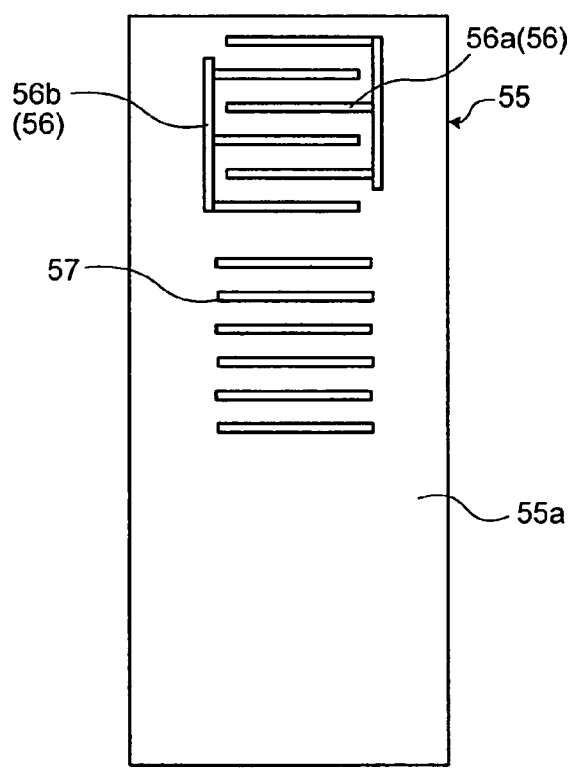
FIG. 28 is a front elevational view of a liquid agitating device according to a sixth embodiment.

A liquid agitating device according to a sixth embodiment of the present invention will be described in detail with reference to FIG. 28. FIG. 28 is a front elevational view of an agitator that amplifies the surface acoustic wave by a grating.

In an agitator 55, a grating 57 is provided at ($\lambda$/2) pitches with respect to the pitch $\lambda$ of each of the comb-shaped electrodes 56a and 56b in the vicinity of a piezoelectric transducer 56 of a substrate 55a as shown in FIG. 28. The grating 57 is a reflecting element with a small reflection coefficient, and obtains a higher reflection coefficient by accumulating effect at Bragg frequency. For example, a conductive strip such as an aluminum thin film may be used as the grating 57. In the agitator 55, the grating 57 is arranged in close proximity to the piezoelectric transducer 56 so that the resonance of the surface acoustic wave generated by the piezoelectric transducer 56 is enhanced (i.e., so that the energy of the surface acoustic wave can be amplified). Thus, a longitudinal wave with extremely large amplitude can be radiated to the liquid, and the effect of liquid agitation can be enhanced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A liquid agitating device, comprising
an agitator comprising a substrate and a sound wave generator that generates a sound wave; and
a container for containing a liquid to be agitated, wherein the container has a bottom wall and a plurality of side walls;
wherein the sound wave generator is arranged on a surface of the substrate that is on an opposite side of the substrate from a surface of the substrate positioned adjacent to a wall surface of the container;
wherein the substrate or an inner wall surface of the container forms a transmitting portion that transmits the sound wave generated by the sound wave generator: and
wherein at least a portion of the transmitting portion is in contact with a liquid, the transmitting portion emits the sound wave towards the liquid at the portion in contact with the liquid, and the sound wave emitted toward the liquid generates a local flow within the liquid and agitates the liquid,
wherein the transmitting portion further includes a sound wave detector that detects the sound wave generated by the sound wave generator, and the sound wave detector includes a processor that performs signal processing on the sound wave detected.

2. A liquid agitating device, comprising
an agitator comprising a substrate and a sound wave generator that generates a sound wave;

a container for containing a liquid to be agitated, wherein the container has a bottom wall and a plurality of side walls;

wherein the sound wave generator is arranged on a surface of the substrate that is on an opposite side of the substrate from a surface of the substrate positioned adjacent to a wall surface of the container;

wherein the substrate or an inner wall surface of the container forms a transmitting portion that transmits the sound wave generated by the sound wave generator; and a processor that performs a signal processing on the sound wave, and the sound wave generator receives a reflected wave of the sound wave, the sound wave being transmitted through the transmitting portion and reflected at an end face, the sound wave generator further outputs the received sound wave to the processor wherein at least a portion of the transmitting portion is in contact with a liquid, the transmitting portion emits the sound wave towards the liquid at the portion in contact with the liquid, and the sound wave emitted toward the liquid generates a local flow within the liquid and agitates the liquid.

3. The liquid agitating device according to claim 1 or 2, wherein
the sound wave generator is formed on a surface of the transmitting portion.

4. The liquid agitating device according to claim 1 or 2 wherein
the sound wave generator is arranged at a position not in contact with the liquid.

5. The liquid agitating device according to claim 1 or 2, wherein
the sound wave generator generates a surface acoustic wave as the sound wave.

6. The liquid agitating device according to claim 5, wherein
in the transmitting portion, transmittivity of the sound wave in a direction of propagation of the sound wave in the portion emitting the sound wave toward the liquid in a portion in the liquid is higher than transmittivity of the sound wave in a portion which is in an ambient gas and from which the sound wave is leaked out to the ambient gas.

7. The liquid agitating device according to claim 1 or 2, wherein
the transmitting portion is in contact with an ambient gas in a portion other than a portion located in the liquid.

8. The liquid agitating device according to claim 7, wherein the ambient gas is air.

9. The liquid agitating device according to claim 7, wherein
in the transmitting portion, the portion emitting the sound wave towards the liquid is present on a liquid side with respect to an air-liquid interface of the ambient gas and the liquid, and an acoustic impedance is discontinuous at the air-liquid interface.

10. The liquid agitating device according to claim 7, wherein
in the transmitting portion, an acoustic impedance of the portion emitting the sound wave toward the liquid is closer to an acoustic impedance of the portion in contact with the ambient gas than to an acoustic impedance of the ambient gas.

11. The liquid agitating device according to claim 7, wherein
in the transmitting portion, a position of the portion emitting the sound wave towards the liquid changes according to a position of an air-liquid interface.

12. The liquid agitating device according to claim 7, wherein
a direction of sound wave emission toward the liquid has a direction component which is opposite to a direction component of a gravitational force.

13. The liquid agitating device according to claim 7, wherein
in the transmitting portion, the position where the sound wave is emitted toward the liquid is an air-liquid interface.

14. The liquid agitating device according to claim 1 or 2, wherein
the transmitting portion has an acoustic impedance which is higher than an acoustic impedance of the liquid, and lower than an acoustic impedance of the sound wave generator.

15. The liquid agitating device according to claim 1 or 2, wherein
in the transmitting portion, the acoustic impedance decreases from a portion of the sound wave generator towards the portion emitting the sound wave towards the liquid.

16. The liquid agitating device according to claim 1 or 2, wherein the transmitting portion is formed of a piezoelectric body.

17. The liquid agitating device according to claim 1 or 2, wherein
in the transmitting portion, the portion emitting the sound wave toward the liquid is located at a different position from a position of the sound wave generator.

18. The liquid agitating device according to claim 1 or 2, further comprising
a controlling device that controls frequency, amplitude, driving time, or a driving timing of the sound wave generator.

19. The liquid agitating device according to claim 1 or 2, wherein
in the transmitting portion, a width of the portion in contact with the liquid and emitting the sound wave toward the liquid is narrower than a width of a portion where the sound wave generator is provided.

20. The liquid agitating device according to claim 19, wherein
in the transmitting portion, a width constantly decreases or monotonously decreases from the portion where the sound wave generator is provided towards the portion emitting the sound wave to the liquid.

21. The liquid agitating device according to claim 20, wherein
in the transmitting portion, the width linearly decreases or exponentially decreases from the portion where the sound wave generator is provided towards the portion emitting the sound wave toward the liquid.

22. The liquid agitating device according to claim 1 or 2, wherein
the sound wave generator is formed in a circular arc shape so that the generated sound wave is focused on a predetermined position in the transmitting portion.

23. The liquid agitating device according to claim 22, wherein
the transmitting portion further includes a waveguide that guides the focused sound wave, and
the sound wave generator focuses the generated sound wave at an inlet of the waveguide.

24. The liquid agitating device according to claim 1 or 2, wherein the transmitting portion further includes a reflector that amplifies the sound wave generated by the sound wave generator.

25. The liquid agitating device according to claim 1 or 2, wherein
in the transmitting portion, at least a part of the transmitting portion is a part of the container containing the liquid.

26. The liquid agitating device according to claim 25, wherein
in the transmitting portion, the portion emitting the sound wave toward the liquid is a part of the container.

27. The liquid agitating device according to claim 25, wherein
an acoustic impedance is discontinuous at an interface between the container and an ambient gas.

28. The liquid agitating device according to claim 1 or 2, wherein
in the transmitting portion, the portion emitting the sound wave toward the liquid extends in a direction of gravitational force.

29. The liquid agitating device according to claim 1 or 2, further comprising a second agitator comprising a transmitting portion, wherein the portion emitting the sound wave towards the liquid extends in a horizontal direction.

30. The liquid agitating device according to claim 1, wherein the transmitting portion further comprises an acoustic matching layer present between the substrate and the container.

31. The liquid agitating device according to claim 30, wherein an impedance of the acoustic matching layer matches an impedance of the substrate and the container.

32. The liquid agitating device according to claim 31, wherein the sound wave generator is arranged on the substrate at a level substantially the same as the level of an air-liquid interface.

33. The liquid agitating device according to any one of the claims 30-32, wherein the substrate is made of a piezoelectric crystalline substrate cut in an optimal crystal orientation.

34. The liquid agitating device according to any one of claims 30-32, wherein the acoustic matching layer is a gel or liquid.

35. The liquid agitating device according to claim 2, wherein the transmitting portion further comprises an acoustic matching layer present between the substrate and the container.

36. The liquid agitating device according to claim 35, wherein an impedance of the acoustic matching layer matches an impedance of the substrate and the container.

37. The liquid agitating device according to claim 36, wherein the sound wave generator is arranged on the substrate at a level substantially the same as the level of an air-liquid interface.

38. The liquid agitating device according to any one of the claims 35-37, wherein the substrate is made of a piezoelectric crystalline substrate cut in an optimal crystal orientation.

39. The liquid agitating device according to any one of claims 35-37, wherein the acoustic matching layer is a gel or liquid.

* * * * *